United States Patent [19]

Vargas et al.

[11] Patent Number: 5,663,388

[45] Date of Patent: Sep. 2, 1997

[54] PROCESS FOR CONVERTING ALDEHYDES TO ACIDS

[75] Inventors: Jose M. Vargas; Magdiel Agosto, both of Baton Rouge, La.

[73] Assignee: Exxon Chemical Patents Inc., Wilmington, Del.

[21] Appl. No.: 269,420

[22] Filed: Jun. 30, 1994

[51] Int. Cl.$^6$ .................................................. C07C 51/16

[52] U.S. Cl. ........................ 554/132; 562/531; 562/534; 562/528

[58] Field of Search ............................ 562/531, 534, 562/528; 554/132

[56] References Cited

U.S. PATENT DOCUMENTS

| 3,321,534 | 5/1967 | Landgraf et al. | 260/638 |
| 4,358,608 | 11/1982 | Shaw et al. | 562/534 |
| 4,649,217 | 3/1987 | Maki et al. | 562/528 |
| 4,778,924 | 10/1988 | Harada | 862/421 |
| 5,306,848 | 4/1994 | Vargas | 568/883 |

Primary Examiner—Deborah D. Carr
Attorney, Agent, or Firm—John J. Mahon; Richard D. Jordan; John F. Hunt

[57] ABSTRACT

A process for forming acids from aldehydes which comprises reacting an oxo aldehyde with water in the presence of an acid-forming catalyst and in the absence of hydrogen, and at a pressure of about 0.1 to 6.99 MPa and a temperature of about 93° to 205° C., thereby converting aldehyde to an oxo acid.

6 Claims, 6 Drawing Sheets

PROCESS FOR CONVERTING ALDEHYDES TO ACIDS

The present invention relates generally to the production of oxo acids from a crude hydroformylation aldehyde product. In particular, it relates to the catalytic conversion of the aldehyde product to oxo acids in the presence of water.

BACKGROUND OF THE INVENTION

Hydroformylation reactions involve the preparation of oxygenated organic compounds by the reaction of carbon monoxide and hydrogen (synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. By way of example, higher alcohols may be produced in the so-called "oxo" process by hydroformylation of commercial $C_5$ to $C_{12}$ olefin fractions to an aldehyde-containing oxonation product, which on hydrogenation yields the corresponding $C_6$ to $C_{13}$ saturated alcohols. The oxo process is the commercial application of the hydroformylation reaction for making higher aldehydes and alcohols from olefins. The crude product of the hydroformylation reaction will typically contain catalyst, aldehydes, alcohols, unreacted olefin feed, synthesis gas and by-products.

The oxo process is well known in the art and is generally described in detail in Kirk-Other, Encyclopedia of Chemical Technology, Volume 16, 3rd edition, John Wiley & Sons, pp. 637–653, 1981.

Thereafter, the product mixture containing the alcohols and aldehydes is recovered and can then be treated by known means to hydrogenate the aldehydes to form additional quantities of the corresponding alcohols. These alcohols, in turn, are widely used as chemical intermediates in the manufacture of plasticizers, detergents, solvents and the like.

Prior to the hydrogenation step, the crude oxo reaction effluent, which contains dissolved cobalt catalysts, the aldehyde and alcohol products and reaction by-products together with any metallic contaminants, is generally treated to remove the dissolved cobalt catalyst, which then for reasons of economy must be recycled to the oxo reactor.

"Demetalled" hydroformylation reaction product or crude oxo alcohol product is the reaction product which is substantially depleted of the transition metal cobalt catalyst required for the hydroformylation reaction. Such crude oxo alcohol product will generally contain cobalt in an amount of from about 0.05 to 3.0 wt. %, calculated as elemental cobalt. The concentration of aldehyde in the crude oxo alcohol product is generally from about 40 to 75 wt. %.

The next step in the oxo process is the hydrogenation of the crude oxo alcohol product which is typically carried out in the presence of hydrogen and at pressures of about 6.89 MPa to 31.00 MPa (1000 to 4500 psig) using sulfided bimetallic cobalt and molybdenum oxides or nickel and molybdenum oxide supported on alumina as the hydrogenation catalyst.

Instead of hydrogenating the crude oxo alcohol product into an alcohol it is sometimes preferable to form an aldehyde intermediate followed by conversion of the crude oxo aldehyde product to an oxo acid. Oxo acids are key reactants for the production of polyol esters, used as components for synthetic lubricant formulations. Such commercial application has potential to utilize branched $C_8$ and $C_9$ acids. Similar commercial application can also utilize linear $C_7$, $C_9$ and $C_{11}$ acids.

In order to commercially produce oxo acids, the hydroformylation process is adjusted to maximize oxo aldehyde formation. This can be accomplished by controlling the temperature, pressure, catalyst concentration, and/or reaction time. Thereafter, the demetalled crude aldehyde product has typically been oxidized according to the reaction below to produce the desired oxo acid:

$$RCHO + \tfrac{1}{2}O_2 \rightarrow RCOOH \tag{1}$$

where R can be a normal or branched alkyl group.

The present inventors have developed a unique process which is capable of producing oxo acids from oxo aldehydes which avoid the inherent dangers associated with using oxygen in a hydrocarbon process stream, while increasing the selectivity of acids verses alcohols. That is, in the absence of hydrogen the catalytic reaction of aldehydes and water favors the formation of acids verses alcohols. Moreover, present inventors have discovered that the use of a catalyst at certain pressures and temperatures will also cause an increase in the selectivity of acids verses alcohols.

The present invention also provides many additional advantages which shall become apparent as described below.

SUMMARY OF THE INVENTION

A process for forming oxo acids from oxo aldehydes preferably comprises the step of reacting the aldehyde with water in the presence of an acid-forming catalyst and in the absence of hydrogen, thereby converting the oxo aldehyde to an oxo acid. The reaction is preferably conducted at a pressure of between about 0.1 MPa to 6.99 MPa, more preferably between about 0.1 MPa to 6.99 MPa, and a temperature of about 93° C. to 205° C., more preferably between about 171° C. to 188° C.

The production of oxo acids from the cobalt catalyzed hydroformylation of an olefinic feedstream preferably comprises the following steps:

(a) hydroformylating the olefinic feedstream by reaction with carbon monoxide and hydrogen in the presence of a hydroformylation catalyst under reaction conditions that promote the formation of an aldehyde-rich crude reaction product;

(b) demetalling the aldehyde-rich crude reaction product to recover therefrom the hydroformylation catalyst and a substantially catalyst-free, aldehyde-rich crude reaction product;

(c) separating the catalyst-free, aldehyde-rich crude reaction product into a concentrated aldehyde-rich product and an aldehyde-poor product;

(d) reacting the concentrated aldehyde-rich product with water in the presence of an acid-forming catalyst and in the absence of hydrogen, thereby converting the concentrated aldehyde-rich product to a crude acid product; and (e) separating the crude acid product into an acid-rich product and an acid-poor product.

The olefinic feedstream is preferably any $C_4$ to $C_{20}$ olefin, more preferably any $C_5$ to $C_{12}$ olefin. The hydroformylation and subsequent reacting of the crude hydroformylation product with water in the presence of an acid-forming catalyst is capable of producing $C_5$ to $C_{21}$ acids, more preferably $C_6$ to $C_{13}$ acids.

Other and further objects, advantages and features of the present invention will be understood by reference to the

3 following specification in conjunction with the annexed drawings, wherein like parts have been given like numbers.

DESCRIPTION OF THE PREFERRED EMBODIMENTS

Oxo acids are key reactants for the production of polyol esters, used as components for synthetic lubricant formulations. Such commercial application has potential to utilize branched $C_8$ and $C_9$ acids. Similar commercial application can also utilize linear $C_7$, $C_9$ and $C_{11}$ acids.

The present invention provides for the production of oxo acids from the cobalt catalyzed hydroformylation of olefins. The oxo acids are preferably formed by the following steps of: (a) hydroformylating $C_4$ to $C_{20}$ olefins by reaction with carbon monoxide and hydrogen in the presence of a cobalt hydroformylation catalyst (e.g., hydrido cobalt carbonyl) under reaction conditions that promote the formation of an aldehyde-rich crude reaction product; (b) demetalling the aldehyde-rich crude reaction product of step (a) to recover therefrom homogeneous cobalt catalyst and to separate therefrom an essentially cobalt-free, aldehyde-rich crude reaction product; (c) separating the cobalt-free, aldehyde-rich crude reaction product into a concentrated aldehyde-rich product and an aldehyde-poor product; (d) reacting the concentrated aldehyde-rich product with water in the presence of an acid-forming catalyst and in the absence of hydrogen, at a temperature in the range between about 93° to 205° C. and a pressure of between about 0.1 to 6.99 MPa, thereby converting the concentrated aldehyde-rich product to a crude acid product; and (e) separating the crude acid product into an acid-rich product and an acid-poor product.

The overall stoichiometry of conversion step (d) can be described by reactions (2) and (3) below:

$$2RCHO + H_2O \rightarrow RCH_2OH + RCOOH \quad (2)$$

$$RCOOH + H_2 \rightarrow RCH_2OH \quad (3)$$

where R can be a normal or branched alkyl group.

The stoichiometry described by reactions (2) and (3), above, can be practiced in the absence of hydrogen to favor reaction (2) and maximize selectivity to the desired acid product. As such, reaction (2) can be considered as two competing steps:

4

$$RCHO + H_2O \rightarrow RCOOH + H_2 \quad (4)$$

$$RCHO + H_2 \rightarrow RCH_2OH \quad (5)$$

Reactions (2) and (3), above, are descriptive of the relevant stoichiometry. Reaction (2) is favored to maximize the desired acid product, when the process concept is practiced in the absence of hydrogen, as indicated in reaction (4). Selectivity to acid production can be further enhanced if a catalyst is chosen such as to favor reaction (4), but to a lesser or no extent at all, reaction (5), above.

The conversion of aldehydes to acids is preferably conducted in the presence of an acid-forming catalyst and $H_2O$, and at a pressure of about 0.1 MPa (0 psig) to 6.99 MPa (1000 psig), more preferably from about 0.1 MPa to 1.48 MPa (200 psig), and at a temperature of between about 93° C. (200° F.) to 205° C. (400° F.), more preferably between about 171° C. (340° F.) to 188° C. (370° F.). It is also preferred that the reaction have a residence time in the reactor of between about 0.5 to 2.0 vvh (volume of catalyst/ (volume of feed/hour)).

ACID-FORMING CATALYST

Any type of catalyst known to one of ordinary skill in the art which is capable of converting oxo aldehydes to oxo acids is contemplated by the present invention. It is even more preferable if the acid-forming catalyst is a supported metallic or bimetallic catalyst.

One such catalyst is a bimetallic nickel-molybdenum catalyst supported on alumina or silica alumina which catalyst has a phosphorous content of about 0.1 wt. % to 1.0 wt. %, based on the total weight of the catalyst. See U.S. patent application, Ser. No. 08/159,099, filed on Nov. 29, 1993, which is incorporated herein by reference. This catalyst is prepared by impregnating molybdenum onto the alumina support using phosphomolybdic acid, $12MoO_3 \cdot H_3PO_4$, as the medium to carry the molybdenum onto the alumina or silica alumina support.

Another catalyst can be prepared by using phosphoric acid as the solvent for the molybdenum salts which are impregnated onto the alumina support. This typically results in phosphorous levels of about 3 wt. % on the catalyst. For example, U.S. Pat. No. 5,151,257 discloses the use of a solution of nickel, carbon and molybdenum oxide in phosphoric acid to prepare a catalyst on the support and U.S. Pat. No. 4,997,801 discloses the same solution on $NiCO_3$ and $MoO_3$ in phosphoric acid (85%) to prepare a catalyst using gamma-alumina as the support.

Still other bimetallic, phosphorous-free Ni/Mo catalyst may be used to convert oxo aldehydes to oxo acids according to the present invention. See U.S. patent application, Ser. No. 08/159,097, filed Nov. 29, 1993, which is incorporated herein by reference. These bimetallic, phosphorous-free Ni/Mo catalysts can be prepared by impregnating an alumina or silica alumina support with an organic acid solution of Ni and Mo salts, the acid being decomposable to $CO_2$ at calcination temperatures of 371° C. (700° F.) to 593° C. (1100° F.). While citric acid is preferred, other suitable organic acids include di- and tri-carboxylic acids having up to about 10 carbon atoms such as oxalic acid, fumaric acid, and maleic acid. Such acids should contain only carbon, hydrogen and oxygen and should be capable of dissolving Ni and Mo salts.

Both of the aforementioned bimetallic catalysts, with and without phosphorous, are also particularly preferred for use in their sulfided form after being sulfided by the techniques well known in the art using gaseous ($H_2S$) or liquid sulfiding compounds, such as ammonium or sodium sulfide solutions, to convert the oxides of the metals to their corresponding sulfides. Typically, about 80% to 100% of the oxides are converted to metal sulfides in such a sulfiding procedure.

It has also been found that carbon supported bimetallic catalyst compositions can produce oxo acids when aldehyde and water are exposed simultaneously to the catalytic surface in the absence of hydrogen. As such, the bimetallic catalysts according the present invention can be impregnated into any support which is capable of allowing catalytic conversion of aldehydes to acid.

Figure 1:
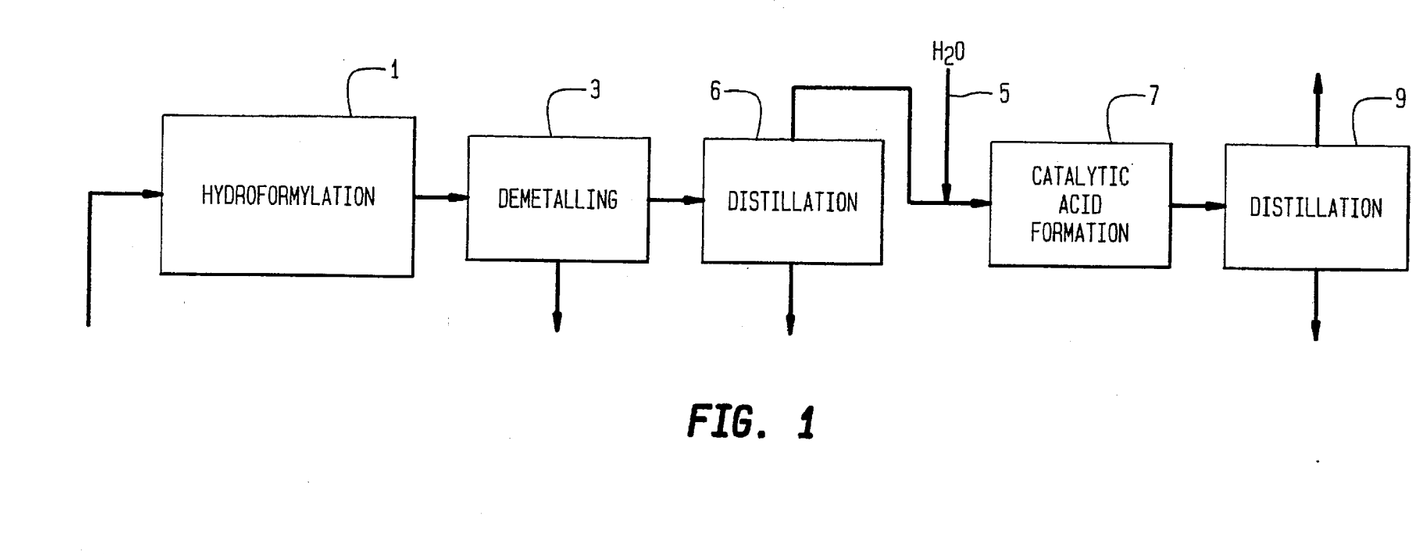
FIG. 1 is a flow diagram of the process according to the present invention wherein oxo acids are formed from demetalled crude oxo aldehyde product.

FIG. 1 demonstrates the primary steps required for forming oxo acids from the crude oxo product of a hydroformylation reaction. An olefinic feedstock (e.g., $C_5$ to $C_{12}$ olefins) are hydroformylated (1) by reaction with carbon monoxide and hydrogen in the presence of a cobalt hydroformylation catalyst (e.g., hydrido cobalt carbonyl) under reaction conditions that promote the formation of an aldehyde-rich crude reaction product. The aldehyde-rich crude reaction product is then demetalled (3) to recover therefrom a homogeneous cobalt catalyst and to separate therefrom essentially cobalt-free crude product which contains 20 wt. % or more of carbonyl-containing compounds such as aldehydes, acetals, ethers and esters. The demetalled, crude hydroformylation product is then separated (6) into a concentrated aldehyde-rich product and an aldehyde-poor product via distillation. Water is added to the essentially cobalt-free crude aldehyde-rich product via conduit 5 and reacted in the presence of an acid-forming catalyst, thereby converting the aldehyde contained within the cobalt-free crude product to a crude acid product (7). Thereafter, the crude acid product is separated into an acid-rich product and an acid-poor product (9).

Figure 2:
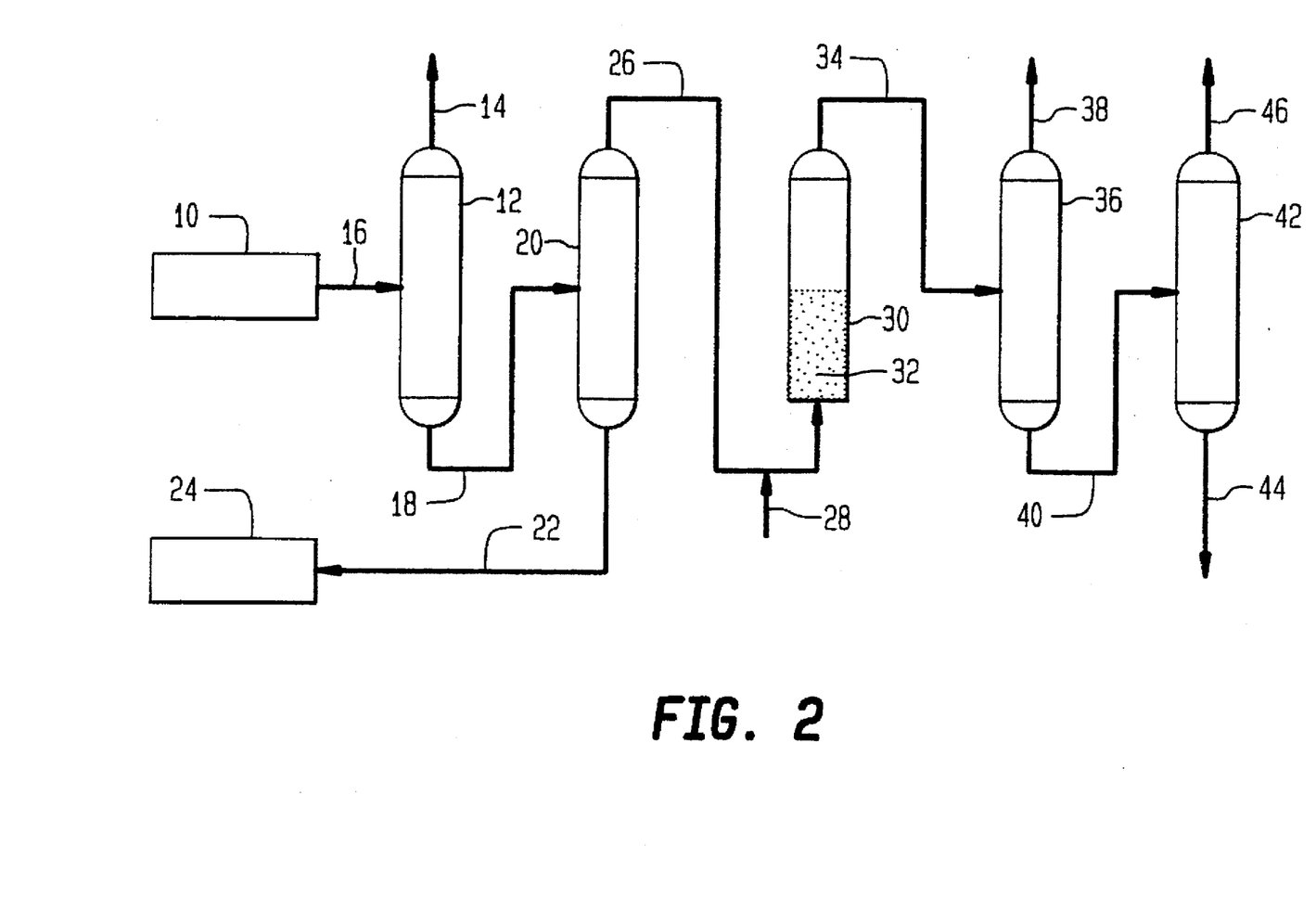
FIG. 2 is a schematic representation of the process for producing oxo acid according to the present invention.

FIG. 2 depicts a more detailed process configuration according to the present invention. In accordance with the present invention an essentially cobalt-free crude aldehyde-rich linear or branched oxo reaction product is delivered via conduit 16 from oxo process 10 to a distillation tower 12 wherein a light oxo fraction (LOF) containing approximately 2–4% aldehyde is taken overhead via conduit 14 and a crude aldehyde product is taken as bottoms via conduit 18 and passed to a distillation tower 20. In distillation tower 20 the crude aldehyde product is separated into a concentrated aldehyde-rich product and an aldehyde-poor product. The aldehyde-poor product (i.e., containing between 5–10% aldehyde) is taken as bottoms via conduit 22 and sent to hydrogenation (24). The aldehyde-rich product is taken overhead via conduit 26 wherein water is added via conduit 28 to form a reaction mixture. The reaction mixture is then passed over an acid-forming catalyst 32 disposed within fixed or trickle bed reactor 30 wherein the aldehydes are converted into the desired oxo acid product (i.e., oxo acid, unconverted oxo aldehyde, oxo alcohol and unconsumed water) via catalytic reaction with water. The crude oxo acid product exits fixed bed reactor 30 overhead via conduit 34 and, optionally, passes through distillation tower 36 wherein an acid-poor product (i.e., unconverted oxo aldehyde, oxo alcohol and unconsumed water) is taken overhead via conduit 38 and an acid-rich product is taken as bottoms via conduit 40. The acid-rich product is then passed from conduit 40 into distillation tower 42 wherein heavies are taken out as bottoms via conduit 44 and an oxo acid product is taken overhead via conduit 46.

Figure 3:
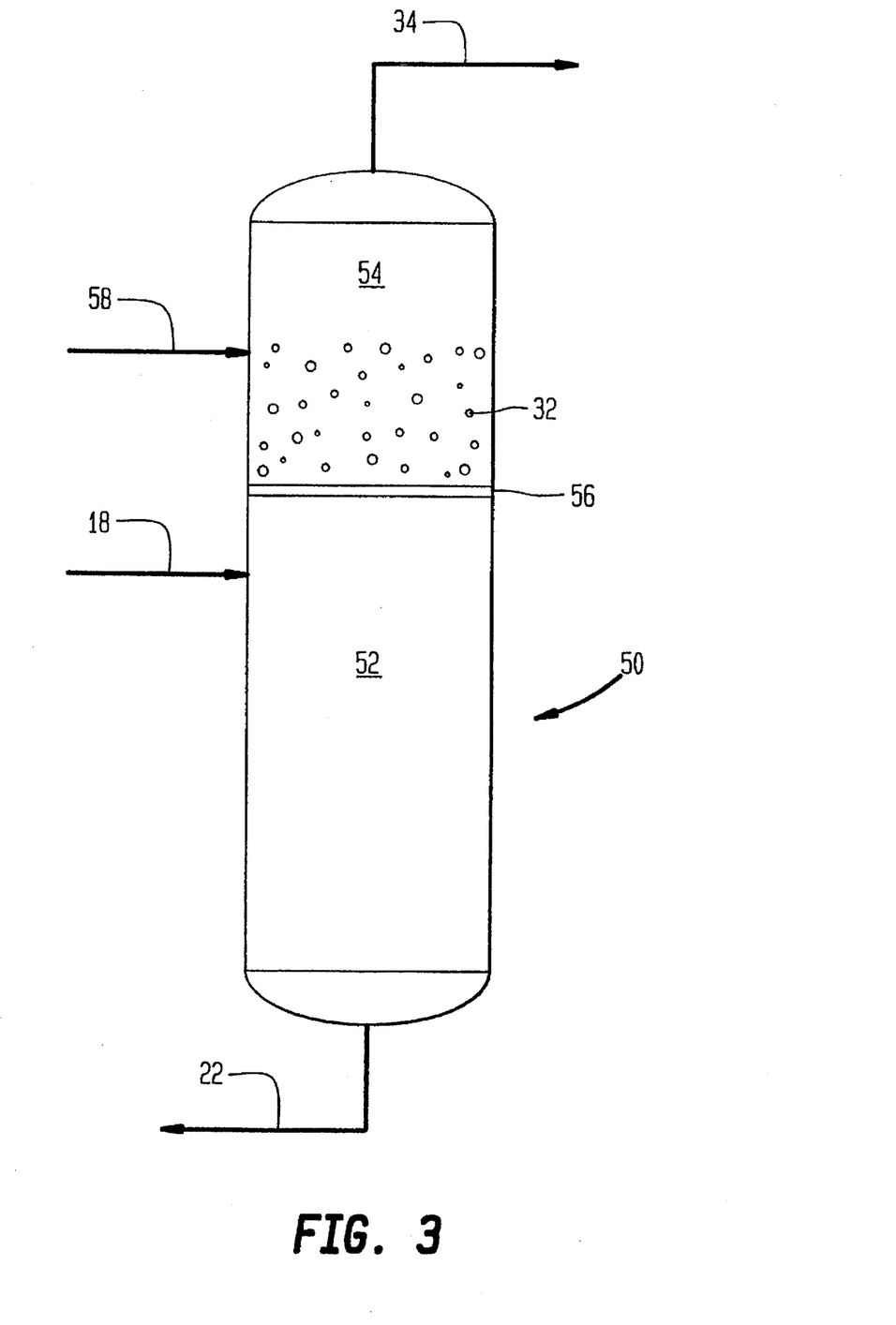
FIG. 3 is a schematic representation of another embodiment according to the present invention wherein the aldehyde distillation and catalytic acid conversion steps are combined into a single reactor.

Optionally, distillation tower 20 and fixed bed reactor 30 from FIG. 2 can be combined into a single dual function reactor 50. As shown in FIG. 3, dual function reactor 50 includes a distillation zone 52 and a catalyst fixed bed zone 54. The crude aldehyde product from conduit 18 is passed from distillation tower 12 to distillation zone 52 wherein an aldehyde-poor product is taken as bottoms via conduit 22 and sent to hydrogenation 24. The aldehyde-rich product then passes through distribution plate 56 where it is passed over an acid-forming catalyst 32 disposed within catalyst fixed bed zone 54 and reacted with water supplied via conduit 58 wherein the aldehydes are converted into the desired oxo acid product. The crude oxo acid product exits dual function reactor 50 overhead via conduit 34 for further downstream processing.

EXAMPLE 1

This example demonstrates acid verses alcohol yield from the reaction of crude (aldehyde-rich, 81 to 83 wt. % aldehyde) oxo aldehyde reaction product and water in the presence of an alumina supported bimetallic nickel-molybdenum catalyst and hydrogen. The test was carried out at 6.89 MPa (1000 psig) over a temperature range of 149° C. (300° F.) to 182° C. (360° F.) Crude nonanal was the feedstock used for catalyst performance evaluation.

Two 316 stainless steel, ½" diameter reactors with appropriate high pressure connectors were each charged with 65 $cm^3$ of catalyst material to be evaluated. The catalyst loaded reactors are immersed in a fluid bed, constant temperature sand bath equipped with electrical heaters for temperature control. Appropriate mechanical connections were installed to allow reactor operation at nominal pressure of 6.99 MPa (1000 psig) and nominal test temperatures of 149° C. (300° F.) and 182° C. (360° F.).

Under steady state conditions liquid feed and gaseous high purity hydrogen (more than 99 volume percent hydrogen) were pumped over the fixed catalyst bed. Liquid and gaseous product was subsequently depressurized and sampled periodically. Aliquots of liquid product and liquid feed were analyzed for composition by gas chromatography.

The liquid feed consisted of demetalled hydroformylation product of crude oxo aldehyde. All evaluations were performed on nonanal which was mixed with water at nominal water/feed of 3 volume percent. The crude oxo aldehyde component distribution for each sample appears in Table 1 below.

TABLE 1

| | (Crude Aldehyde (Nonanal) Feed Composition) | | | | |
|---|---|---|---|---|---|
| Sample No. | Lights, wt. % (Olefin + Paraffin) | Aldehyde + Formate Esters, wt. % | Alcohol, wt. % | Heavy Acid, Wt. % | Heavier than Acid, wt. % |
| 1 | 6.79 | 81.20 | 4.05 | 2.96 | 5.00 |
| 2 | 6.59 | 83.22 | 4.07 | 2.65 | 3.47 |
| 3 | 6.05 | 83.45 | 3.57 | 2.65 | 4.27 |
| 4 | 7.13 | 85.45 | 4.02 | 1.70 | 1.69 |

For this particular example, an alumina supported sulfided Ni/Mo catalyst was charged as test material. This catalyst is a bimetallic Ni/Mo on alumina catalyst containing about 3 weight percent phosphorous. Typical catalyst properties are included in Table 2 below.

TABLE 2

(Representative Ni/Mo Catalyst Properties)

| Chemical Composition Component Weight % * | | | | Physical Properties | |
|---|---|---|---|---|---|
| MoO$_3$ | NiO | P | Support Type | Surface Area m$^2$/g | Total Pore Volume, ml/g |
| 20.0 | 4.0 | 2.85 | Al$_2$O$_3$ | 180 | 0.45 |

*denotes a balanced chemical composition of Al$_2$O$_3$ and SiO$_2$.

The catalyst was tested at the conditions set forth below in Table 3. All tests were conducted at a nominal feed rate of 130 ml/hr, a water rate of 4 ml/hr, a linear hourly space velocity (LHSV) of 1 ml catalyst/(ml feed/hr), and at 6.99 MPa (1000 psig). Product composition for different test samples included in Table 4 was determined by gas chromatography.

TABLE 3

(Test Conditions)

| Sample No. | H$_2$ | Temperature (°C.) |
|---|---|---|
| 1 | Yes | 148.89 |
| 2 | Yes | 182.22 |

TABLE 4

(Product Composition)

| Sample No. | Lights (wt %) | Aldehyde + Formate Esters (wt %) | Alcohol (wt %) | Heavy Acid (wt %) | Heavier than Acid (wt %) |
|---|---|---|---|---|---|
| 1 | 6.38 | 0.18 | 75.90 | 7.53 | 10.00 |
| 2 | 7.45 | 0.31 | 76.15 | 7.18 | 8.92 |

TABLE 5

(Product Yield)

| Sample No. | Delta Acid* (wt %) | Delta Heavier Than Acid** (wt %) |
|---|---|---|
| 1 | 4.57 | 5.00 |
| 2 | 4.53 | 5.45 |

*Calculated as product heavy acid composition minus feed heavy acid composition.
**Calculated as product heavy composition minus feed heavy composition.

The catalyst's hydrogenation performance is assessed by studying aldehyde conversion as well as selectivity to by-products. Comparing product composition in Table 4 with the corresponding feed crude nonanal composition in Table 1, aldehyde conversion in excess of 95% is obtained. Alcohol and acid products from the acid conversion process according to the present invention are indicated in Table 4 above. Alcohol production selectivity was preferred in this example, as hydrogen promoted conversion to alcohol product through reaction of oxo acids with hydrogen. Thus, the alcohol content for samples 1 and 2 is about one order of magnitude higher than the corresponding acid product composition.

EXAMPLE 2

This example demonstrates catalytic oxo acid production over an alumina supported Ni/Mo catalyst resulting from the catalytic reaction of oxo aldehyde and H$_2$O in the absence of hydrogen. Test conditions are identical to those described in Example 1, above, but in the absence of hydrogen. Crude nonanal was the feedstock used for catalyst performance evaluation.

The catalyst's ability to convert the oxo aldehydes of Samples 3 and 4 (see Table 1) and water into oxo acids is set forth below in Tables 6–8.

TABLE 6

(Test Conditions)

| Sample No. | H$_2$ | Temperature (°C.) |
|---|---|---|
| 3 | No | 148.89 |
| 4 | No | 182.22 |

TABLE 7

(Product Composition)

| Sample No. | Lights (wt %) | Aldehyde + Formate Esters (wt %) | Alcohol (wt %) | Heavy Acid (wt %) | Heavier than Acid (wt %) |
|---|---|---|---|---|---|
| 3 | 5.53 | 35.93 | 19.64 | 23.79 | 15.11 |
| 4 | 7.46 | 14.88 | 26.17 | 30.99 | 20.49 |

TABLE 8

(Product Yield)

| Sample No. | Delta Acid* (wt %) | Delta Heavier Than Acid** (wt %) |
|---|---|---|
| 3 | 21.14 | 10.82 |
| 4 | 29.29 | 18.80 |

*Calculated as product heavy acid composition minus feed heavy acid composition.
**Calculated as product heavy composition minus feed heavy composition.

Figure 4:
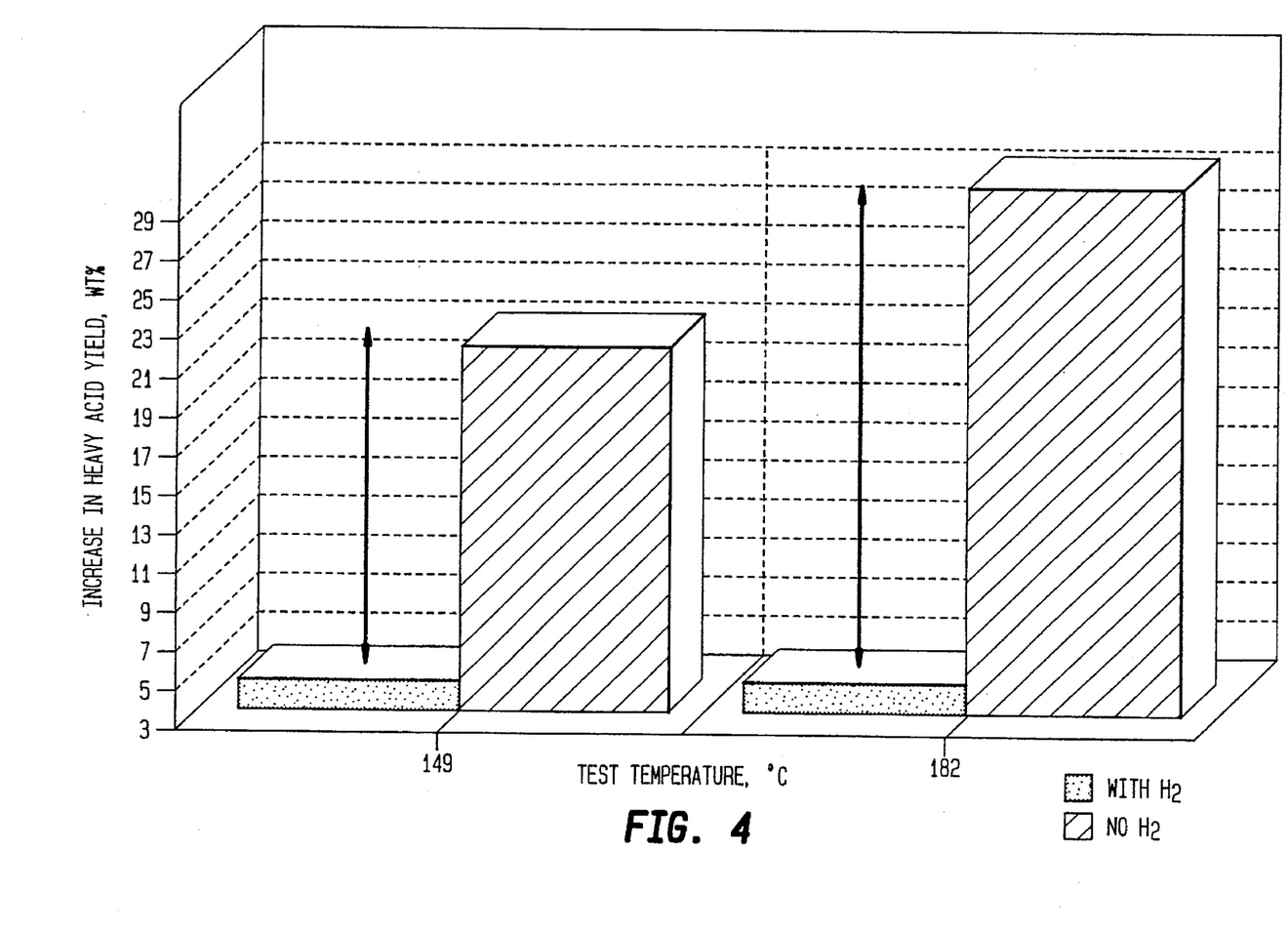
FIG. 4 is a graph plotting yields for catalytic acid production from crude nonanal feedstock with and without hydrogen.

By comparison of product composition in Table 7, aldehyde catalytically reacts with water in the absence of hydrogen to cause significant selectivity in oxo acid production, relative to Samples 1 and 2 of Example 1 which were conducted in the presence of hydrogen. Thus the catalytic reaction of aldehyde and water in the absence of hydrogen has a threefold improvement in selectivity to oxo acid product, relative to the competitive simultaneous occurrence of reaction (2) and (3), above. The relative increase in oxo acid yield is graphically presented in FIG. 4.

EXAMPLE 3

This example demonstrates catalytic acid yield when crude aldehyde is reacted with water over bimetallic sulfided Ni/Mo on carbon. The test was carried out at 1.0 MPa (150 psig) over a temperature range of 149° C. (300° F.) to 199° C. (390° F.). Crude heptanal and nonanal were the feedstocks used to evaluate catalyst performance.

Two 316 stainless steel, ½" diameter reactors with appropriate high pressure connectors were each charged with 65 cm³ of catalyst material to be evaluated. The catalyst used was a sulfided Ni/Mo on carbon catalyst having 20 wt. % $MoO_3$, 4 wt. % NiO, a surface area of 1000 m²/g, and a total pore volume of 0.6 ml/g. The catalyst loaded reactors are immersed in a fluid bed, constant temperature sand bath equipped with electrical heaters for temperature control. Appropriate mechanical connections were installed to allow reactor operation at nominal pressure of 1.13 MPa (150 psig) and nominal test temperatures of 149° C. (300° F.) and 199° C. (390° F.).

Under steady state conditions liquid feeds, crude aldehyde and water, were pumped over the fixed catalyst bed. Liquid and gaseous product was subsequently depressurized and sampled periodically. Aliquots of liquid product and liquid feed were analyzed for composition by gas chromatography.

The liquid feed consists of demetalled hydroformylation product, i.e., crude aldehyde. All evaluations were performed on crude heptanal and nonanal, mixed with water at nominal water/feed of 12 vol. %. Typical crude aldehyde component distribution appears in Table 9, below.

TABLE 9

(Crude Aldehyde Feed Composition)

| Sample No. | Lights, wt. % (Olefin + Paraffin) | Aldehyde + Formate Esters, wt. % | Alcohol, wt. % | Heavy Acid, Wt. % | Heavier than Acid, wt. % |
|---|---|---|---|---|---|
| Heptanal | | | | | |
| 1 | 1.09 | 56.37 | 9.61 | 7.11 | 25.82 |
| 2 | 1.52 | 43.87 | 12.81 | 1.90 | 39.90 |
| 3 | 1.60 | 43.47 | 11.32 | 1.75 | 41.86 |
| Nonanal | | | | | |
| 4 | 7.49 | 85.35 | 2.67 | 2.05 | 2.44 |
| 5 | 7.37 | 85.68 | 2.50 | 2.02 | 2.43 |
| 6 | 7.54 | 85.59 | 2.62 | 1.99 | 2.26 |
| 7 | 7.61 | 85.19 | 2.57 | 2.25 | 2.38 |

The catalyst was tested at conditions listed in Table 10, below. All tests were run at a nominal feed rate of 130 ml/hr and the water rate was 12 volume % water per feed. Tests at 2 hours space time had a nominal feed rate of 65 ml/hr. Product composition and product yield for the different test samples are set forth in Tables 11 and 12, respectively. The product composition was determined by gas chromatography.

TABLE 10

(Test Conditions)

| Sample No. | Space Time (hr) | Temperature (°C.) |
|---|---|---|
| 1 | 1.0 | 148.89 |
| 2 | 1.0 | 182.22 |
| 3 | 1.0 | 198.89 |
| 4 | 1.0 | 148.89 |
| 5 | 1.0 | 182.22 |
| 6a | 0.5 | 182.22 |
| 6b | 1.0 | 182.22 |
| 7a | 1.0 | 182.22 |
| 7b | 2.0 | 182.22 |

TABLE 11

(Product Composition)

| Sample No. | Lights (wt %) | Aldehyde + Formate Esters (wt %) | Alcohol (wt %) | Heavy Acid (wt %) | Heavier than Acid (wt %) |
|---|---|---|---|---|---|
| 1 | 1.33 | 45.81 | 26.31 | 18.32 | 8.23 |
| 2 | 2.79 | 15.84 | 44.50 | 20.53 | 16.34 |
| 3 | 3.85 | 10.46 | 39.10 | 16.16 | 30.43 |
| 4 | 6.92 | 46.07 | 16.33 | 22.92 | 7.76 |
| 5 | 7.28 | 18.92 | 27.20 | 35.54 | 11.06 |
| 6a | 6.77 | 35.05 | 22.45 | 28.83 | 6.90 |
| 6b | 7.72 | 18.69 | 26.99 | 36.04 | 10.56 |
| 7a | 7.46 | 20.36 | 25.48 | 35.33 | 11.37 |
| 7b | 8.19 | 8.23 | 27.61 | 38.08 | 17.89 |

TABLE 12

(Product Yield)

| Sample No. | Delta Acid* (wt %) | Percent Aldehyde Conversion** |
|---|---|---|
| 1 | 11.21 | 18.7 |
| 2 | 18.63 | 63.9 |
| 3 | 14.41 | 75.9 |
| 4 | 20.87 | 46.0 |
| 5 | 33.52 | 77.9 |
| 6a | 26.84 | 59.0 |
| 6b | 34.05 | 78.2 |
| 7a | 33.08 | 76.1 |
| 7b | 35.83 | 90.3 |

*Calculated as product heavy acid composition minus feed heavy acid composition.
**Calculated as [product aldehyde composition] minus [feed heavy acid composition] divided by [feed aldehyde composition] times 100.

The production of oxo acid using a Ni/Mo on carbon catalyst was assessed by studying aldehyde conversion as well as selectivity to by-products. As indicated in Tables 10 and 11, various levels of aldehyde conversion can be attained at different temperature and space time combinations.

Higher levels of oxo acid are produced when the feedstock is crude linear nonanal (i.e., acid increased in the range of 26 wt. % to 35 wt. %) relative to heptanal (acid increased in the range of 11 wt. % to 14 wt. %). The two to three-fold difference in acid producing capacity for nonanal relative to heptanal is proportional to aldehyde content in the crude feedstocks, i.e., nonanal contains about twice as much aldehyde as heptanal.

Figure 5:
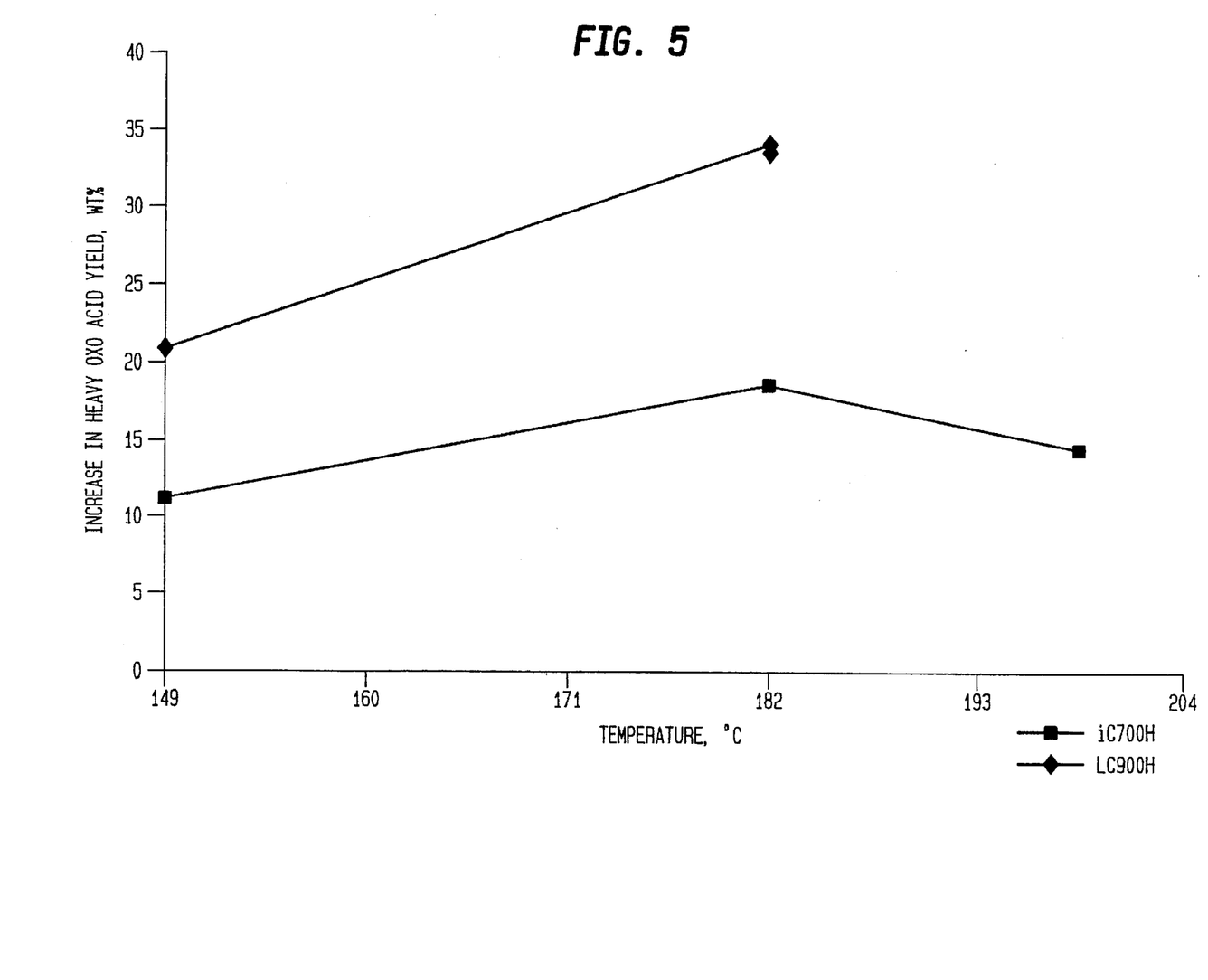
FIG. 5 is a graph showing the yields for catalytic acid production from crude heptanal feedstock and crude nonanal feedstock.
Figure 6:
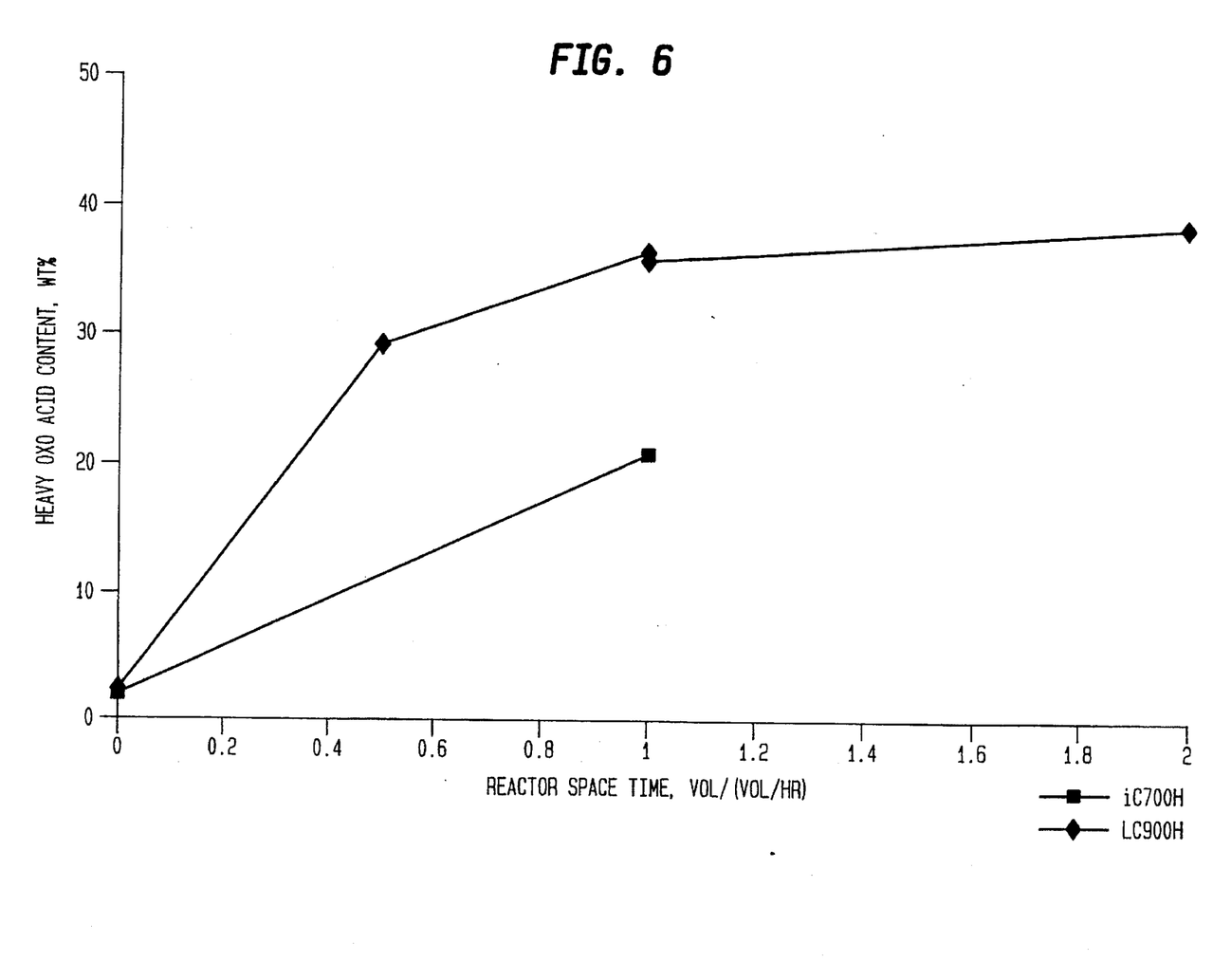
FIG. 6 is a graph showing the weight percents for catalytic acid production from crude heptanal feedstock and crude nonanal feedstock.

Optimum conditions for maximized acid production can be obtained by adjusting temperature (FIG. 5) and reactor residence time (FIG. 6). As such, as indicated in FIG. 5, 182° C. (360° F.) is an optimum temperature for acid production at test conditions. Similarly, as indicated in FIG. 6, not much further acid production is attained at reactor residence times higher than 1 vvh (volume catalyst/(volume feed/hour)).

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for forming acids from aldehydes which comprises reacting said aldehyde with water in the presence of a supported bimetallic catalyst at a temperature in the range between about 171° C. to 188° C. and in the absence of hydrogen, thereby converting said aldehyde to said acid.

2. The process according to claim 1 wherein said reaction is conducted at a pressure of between about 0.1 MPa to 6.99 MPa.

3. The process according to claim 2 wherein said pressure is 0.1 MPa to 1.48 MPa.

4. The process according to claim 1 wherein said supported bimetallic catalyst is selected from the group consisting of: a bimetallic catalyst supported on alumina or silica alumina which catalyst has a phosphorous content of about 0.1 wt. % to 1.0 wt. %, based on the total weight of the catalyst; a bimetallic catalyst supported on alumina or silica alumina which catalyst has a phosphorous content of about 3 wt. % on the catalyst; a bimetallic, phosphorous-free catalyst supported on alumina or silica alumina; a bimetallic sulfided catalyst, with or without phosphorous; and a carbon supported bimetallic catalyst.

5. The process according to claim 4 wherein said bimetallic catalyst is a nickel-molybdenum catalyst.

6. The process according to claim 1 wherein said reaction occurs for between about 0.5 to 2.0 vvh.

* * * * *